(12) United States Patent
Howell

(10) Patent No.: US 7,787,123 B2
(45) Date of Patent: Aug. 31, 2010

(54) TWO LINE GAS SPECTROSCOPY CALIBRATION

(75) Inventor: James Howell, Louisville, CO (US)

(73) Assignee: Zolo Technologies, Inc., Boulder, CO (US)

( * ) Notice: Subject to any disclaimer, the term of this patent is extended or adjusted under 35 U.S.C. 154(b) by 286 days.

(21) Appl. No.: 12/067,789

(22) PCT Filed: Oct. 4, 2006

(86) PCT No.: PCT/US2006/038933

§ 371 (c)(1),
(2), (4) Date: May 15, 2008

(87) PCT Pub. No.: WO2007/041670

PCT Pub. Date: Apr. 12, 2007

(65) Prior Publication Data

US 2008/0204720 A1      Aug. 28, 2008

Related U.S. Application Data

(60) Provisional application No. 60/723,761, filed on Oct. 4, 2005.

(51) Int. Cl.
*G01N 21/39* (2006.01)

(52) U.S. Cl. .............. 356/437; 356/51; 250/339.13; 250/343

(58) Field of Classification Search ......... 356/437, 356/438, 439; 250/343, 347, 339.13
See application file for complete search history.

(56) References Cited

U.S. PATENT DOCUMENTS

| 5,813,767 A | 9/1998 | Calabro |
| 7,248,755 B2 | 7/2007 | Sappey et al. |
| 2002/0031737 A1 | 3/2002 | Von Drasek |

FOREIGN PATENT DOCUMENTS

| WO | WO 2004/090496 A2 | 3/2004 |
| WO | WO 2004/090496 A3 | 3/2004 |

OTHER PUBLICATIONS

Teichert, et al. (2003) "Simultaneous in situ Measurement of CO, $H_2O$, and Gas Temperature in a Full-Sized, Coal-Fired Power Plant by Near-Infrared Diode Lasers" Applied Optics, 42(12):2043.

Sanders et al., (2001) "Diode-laser Absorption Sensor for Line-of-Sight Gas Temperature Distributions" Applied Optics 40(24):4404-4415.

*Primary Examiner*—F. L Evans
(74) *Attorney, Agent, or Firm*—Swanson & Bratschun, L.L.C.

(57) ABSTRACT

A method of calibrating an absorption spectroscopy measurement wherein the calibration method includes projecting laser light through a sample of a first quantity of a gas of interest and a second irrelevant quantity of a spectroscopically identical or similar gas (10). The first and second spectroscopic absorptions of the laser light are measured over specific first and second absorption lines. A functional relationship is determined between the first and second measured spectroscopic absorptions and two unknown variables. The function relationships may then be simultaneously solved to determine one or both unknown variables and thereby obtain a measurement relating to the first quantity of the gas of interest, calibrated for the second irrelevant quantity of gas.

10 Claims, 2 Drawing Sheets

TWO LINE GAS SPECTROSCOPY CALIBRATION

Related Application

This application is a 35 USC §371 of PCT Application Ser. No. PCT/US2006/38933, filed Oct. 4, 2006, currently pending, entitled "Two Line Gas Spectroscopy Calibration", which claims priority to U.S. Provisional Application Ser. No. 60/723,761, filed Oct. 4, 2005, entitled "Two Line Oxygen Purge Air Calibration," which are each incorporated herein in their entirety by reference.

TECHNICAL FIELD

The present invention is directed toward a method and apparatus for calibrating an absorption spectroscopy system and more particularly toward a method and apparatus for determining a gas concentration within a combustion chamber using tunable diode laser absorption spectroscopy in installations where supplemental gas is present in the spectroscopy path.

BACKGROUND ART

A large percentage of the electrical power generated in the United States of America is created in coal combustion power plants. The bulk of worldwide electricity production similarly relies on coal as a primary energy source. It is likely that coal will remain a primary energy source in the foreseeable future given the long term environmental concerns with the storage of waste from nuclear energy generation operations, and the inefficiencies associated with solar powered electrical generation. In addition vast worldwide coal reserves exist sufficient for at least 200 years of energy production at current rates.

There is and will continue to be, however, a high demand to reduce the emissions of pollutants associated with coal fired electrical energy generation, and to increase the overall efficiency of the coal fired generation process. The monitoring of the $O_2$ and other gas levels within a combustion chamber or power plant furnace is one key component of efficiency monitoring and control. Traditionally, in power plants and other industrial combustion settings the efficiency of the combustion process and the level of pollution emission have been determined indirectly through measurements taken on extracted gas samples with techniques such as non-dispersive infrared (NDIR) photometry. Extractive sampling systems are not particularly well suited to closed loop control of a combustion process since a significant delay can be introduced between the time of gas extraction and the ultimate analysis. In addition, extractive processes generally result in a single point measurement which may or may not be representative of the actual concentration of the measured species within what can be a highly variable and dynamic combustion process chamber.

Laser based optical species sensors have recently been implemented to address the concerns associated with extraction measurement techniques. Laser based measurement techniques can be implemented in situ and offer the further advantage of high speed feedback suitable for dynamic process control. A particularly promising technique for measuring combustion gas composition, temperature and other combustion parameters is tunable diode laser absorption spectroscopy (TDLAS). TDLAS is typically implemented with diode lasers operating in the near-infrared and mid-infrared spectral regions. Suitable lasers have been extensively developed for use in the telecommunications industry and are, therefore, readily available for TDLAS applications. Various techniques of TDLAS which are more or less suitable for the sensing and control of combustion processes have been developed. Commonly known techniques are wavelength modulation spectroscopy, frequency modulation spectroscopy and direct absorption spectroscopy. Each of these techniques is based upon a predetermined relationship between the quantity and nature of laser light received by a detector after the light has been transmitted through a combustion process chamber and absorbed in specific spectral bands which are characteristic of the gases present in the process or combustion chamber. The absorption spectrum received by the detector is used to determine the quantity of the gas species under analysis plus associated combustion parameters such as temperature.

For example, Von Drasek et al., United States Patent Application Serial Number 2002/0031737A1, teaches a method and apparatus of using tunable diode lasers for the monitoring and/or control of high temperature processes. Von Drasek features the use of direct absorption spectroscopy to determine the relative concentration of numerous combustion species, temperature and other parameters. Calabro, U.S. Pat. No. 5,813,767, teaches a similar system for monitoring combustion and pollutants developed in a combustion chamber. Calabro utilizes an indirect spectroscopy technique wherein observed Doppler broadening of the shape of an absorption feature serves as the basis for temperature analysis.

Teichert, Fernholz, and Ebert have extended the use of TDLAS as a known laboratory analysis technique to a workable field solution suitable for the sensing of certain combustion parameters within the furnace of a full sized coal fired power plant. In their article, "Simultaneous in situ Measurement of CO, $H_2O$, and Gas Temperature in a Full-Sized, Coal-Fired Power Plant by Near-Infrared Diode Lasers," (Applied Optics, 42(12):2043, 20 Apr. 2003) the authors present a successful implementation of direct absorption spectroscopy at a coal fired power plant and discuss certain technical challenges resulting from the extremely large scale and violent nature of the coal burning process. In particular, typical coal fired power plants have combustion chamber diameters of 10-20 meters. The plants are fired by pulverized coal, which results in a combustion process which both obscures the transmission of laser light because of the high dust load and which is extremely luminous. In addition, various strong disturbances are found under power plant combustion conditions. The overall transmission rate of light through the process chamber will fluctuate dramatically over time as a result of broadband absorption, scattering by particles or beam steering owing to refractive-index fluctuations. There is also intense thermal background radiation from the burning coal particles which can interfere with detector signals. The environment outside of the power plant boiler also makes the implementation of a TDLAS sensing or control system problematic. For example, any electronics, optics or other sensitive spectroscopy components must be positioned away from intense heat, or adequately shielded and cooled. Even though the implementation of a TDLAS system is extremely difficult under these conditions, TDLAS is particularly well suited to monitor and control a coal combustion process. A comprehensive discussion of the use of TDLAS to monitor and control a combustion process is contained in commonly assigned and copending PCT Application Serial Number PCT/US04/010048, filed Mar. 31, 2004, entitled METHOD AND APPARATUS FOR THE MONITORING AND CONTROL OF COMBUSTION, which application is incorporated herein by reference in its entirety.

Typically, the electronic, optical, and other sensitive spectroscopy components which must communicate with the interior of a combustion chamber are associated with a special opening into the combustion chamber. This opening or port will often feature a quartz, fused silica, or other window fabricated from a transparent material which is stable at the extremely high temperatures associated with the interior of the combustion chamber. Alternatively, the opening may not include a transparent window. In either case, the opening in a typical coal fired power plant must transverse the furnace wall and may be about 18 inches long. As described above, the interior of the combustion chamber is an extremely hostile environment full of pulverized coal, ash, and other particulate matter. Thus, there is a tendency for the opening or port to become clogged or partially blocked with ash and other particulate matter.

Port blockage can be addressed by flowing purge air through the port. The purge air may be constantly flowed through the port from a captive purge gas supply or, more commonly, ambient air from outside of the combustion chamber may be utilized Typically, purge air will thus include significant amounts of $O_2$ relative to the $O_2$ levels within the combustion chamber.

It is useful to monitor the $O_2$ or other gas levels as part of the TDLAS monitoring and control of a combustion process. The introduction of $O_2$ containing purge gas significantly complicates this measurement. Depending on the location in the furnace where a measurement is taken, the purge gas may include anywhere from 30% to 60% of the total $O_2$ present along a TDLAS path. Only the $O_2$ in the furnace is of interest for proper combustion control. Similarly any absorption spectroscopy measurement of a quantity of gas is complicated if a second quantity of the gas is also present in the measurement path. Thus a need exists for a method to accurately quantify the effect of purge gas $O_2$ on the desired combustion chamber $O_2$ measurement. The present invention is directed to overcoming one or more of the problems discussed above.

SUMMARY OF THE INVENTION

One aspect of the present invention is a method of calibrating an absorption spectroscopy measurement where the probe laser path transverses both a quantity of the gas of interest, and a quantity of a spectroscopically similar or identical gas which is irrelevant to the desired measurement, but has the potential interfere with the measurement. The calibration method includes projecting laser light through a sample containing a first quantity of a gas of interest and a second irrelevant quantity of a spectroscopically identical or similar gas. The method also includes measuring first and second spectroscopic absorption of the laser light over specific first and second absorption lines. A functional relationship is determined between the first and second measured spectroscopic absorptions and two unknown variables. The functional relationships may then be simultaneously solved to determine one or both unknown variables and thereby to obtain a measurement relating to the first quantity of the gas of interest, calibrated for the second irrelevant quantity of gas.

The method may also include the determination of physical parameters such as calculating a mean temperature within the first quantity of the gas of interest, measuring a path length through the first quantity of the gas of interest or measuring a second path length through the second quantity of a spectroscopically identical or similar gas. The functional relationships may be determined with respect to these measured parameters.

The functional relationships may also be determined with respect to known physical constants including, but not limited to a first select absorption line strength associated with the first select absorption line, a second select absorption line strength associated with the second select absorption line, a lower energy state associated with the first select absorption line a lower energy state associated with the second select absorption line; and a gas concentration of the gas of interest contained within the second quantity of a spectroscopically identical or similar gas.

One embodiment of the present invention is a method of determining the $O_2$ or other gas of interest concentration within a combustion chamber using tunable diode laser absorption spectroscopy (TDLAS) where at least one laser is positioned to transmit laser light through at least one opening into a combustion chamber, and where an $O_2$ containing purge gas flow is applied to the opening. The method includes projecting laser light through the opening and through the combustion vessel, measuring first and second spectroscopic absorptions of the laser light over first and second select $O_2$ absorption lines. In addition, a first functional relationship between the first measured spectroscopic absorption and two unknown variables, namely the temperature of the $O_2$ containing purge gas and the $O_2$ concentration within the combustion chamber, is determined. Similarly, a second functional relationship between the second measured spectroscopic absorption and the two unknown variables is determined Finally, the first and second functional relationships may be solved to determine the $O_2$ concentration within the combustion chamber.

The method may also include calculating a temperature within the combustion chamber, measuring a path length through the combustion chamber, and measuring a purge path length associated with any opening. In this aspect of the invention, the first and second functional relationships are determined with respect to the measured temperature within the combustion chamber, the measured path length through the combustion chamber, and the measured purge path length, as well as the unknown variables discussed above. The determination of the first and second functional relationships may be made with respect to known physical constants including the first and second select $O_2$ absorption line strengths, the lower energy states associated with each $O_2$ absorption line selected, and the $O_2$ concentration of the $O_2$ containing purge gas flow.

The temperature within the combustion chamber may be calculated by any suitable method, however, this temperature may be calculated from the absorption spectrum additionally measured over at least two $H_2O$ absorption lines.

The first and second select $O_2$ absorption lines may be selected from all possible $O_2$ absorption lines, however, the line associated with the absorption of light having a wavelength of 760.258 nm and the line associated with the absorption of light having a wavelength of 760.455 nm are particularly well suited for use as the first and second select $O_2$ absorption lines.

Another aspect of the present invention is an apparatus for determining the $O_2$ concentration within a combustion chamber. The apparatus includes at least one opening into the combustion chamber, a tunable diode laser positioned to transmit light through the opening and the combustion chamber, and a source of $O_2$ containing purge gas in fluid communication with the opening. Also included in the apparatus are means for measuring a first spectroscopic absorption line, a second spectroscopic absorption line, and for determining functional relationships and solving the relationships for the O₂ concentration within the combustion chamber, all as described above.

DETAILED DESCRIPTION OF THE PREFERRED EMBODIMENT

Figure 1:
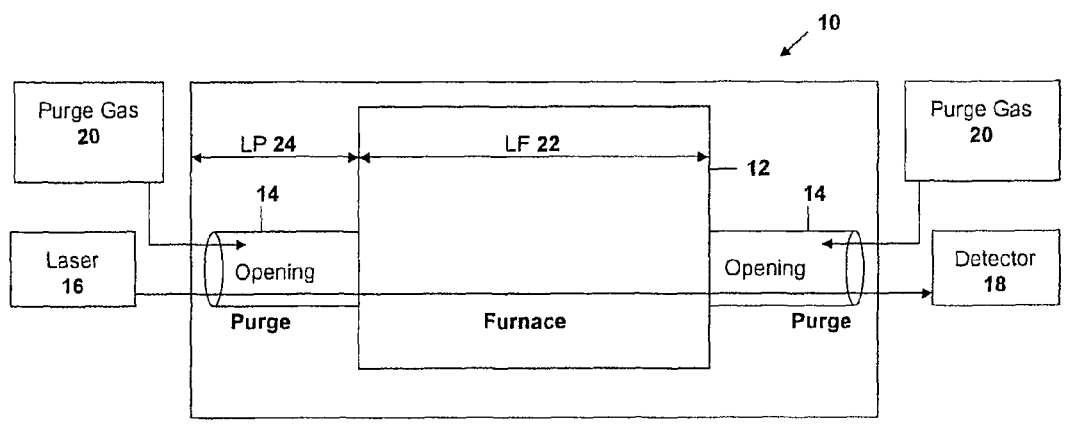
FIG. 1 is a schematic diagram of an apparatus consistent with the present invention.

An apparatus 10 suitable for implementation of the present invention is shown in the block diagram of FIG. 1. The apparatus 10 includes a combustion chamber 12, which is shown in FIG. 1 as the furnace of a coal fired power plant. Access to the interior of the combustion chamber 12 is provided by one or more openings 14 formed in the walls of the combustion chamber 12. A laser 16 suitable for performing tunable diode laser absorption spectroscopy (TDLAS) is associated with the combustion chamber 12 and positioned at an opening 14 such that the laser 16 may project laser light through the opening 14 and combustion chamber 12, all as shown in FIG. 1. Opposite the combustion chamber 12 from the laser 16 is a detector 18 which is shown as associated with a second opening 14. Alternatively, the detector 18 could be associated with the same opening 14 as the laser 16 with the laser light being received after a reflected double pass through the combustion chamber 12.

The environment within a combustion chamber 12 is extremely hostile. A coal fired power plant, for example, is fed by pulverized coal which is blown into the combustion chamber 12 at an extremely high rate. Thus, the combustion chamber 12 is a maelstrom of coal dust, ash, and other particulate matter. These particulates will quickly clog any opening 14 associated with the combustion chamber 12 or coat and obscure any window associated with the opening 14.

An opening 14 may be maintained in a relatively unobscured manner by flowing purge gas from a purge gas source 20 through the opening 14 and into the combustion chamber 12, thus actively clearing dust, ash, and other particulate matter. The purge gas source 20 may be a self contained unit holding a select gas under pressure. More typically, the purge gas source 20 will merely be a compressor feeding air from outside the combustion chamber 12 through any opening 14. As discussed in detail below, if air or other O₂ containing purge gas is utilized, O₂ is introduced directly into the probe path of the laser 16. The introduction of O₂ directly into the probe path complicates a desired measurement of O₂ concentration within the combustion chamber 12.

The present invention is primarily described as an apparatus and method for calibrating the TDLAS measurement of gas concentrations or temperatures within a combustion chamber where the same or a spectroscopically similar gas is introduced to purge an opening. The invention is not limited to such embodiments however. The calibration method may be applied to any spectroscopic analysis implementation where light is transmitted through a region containing a gas of interest, and also through a region containing a quantity of other gas which could provide a false signal. Thus the calibration aspects of the invention have broad application to any implementation of gas absorption spectroscopy.

Figure 2:
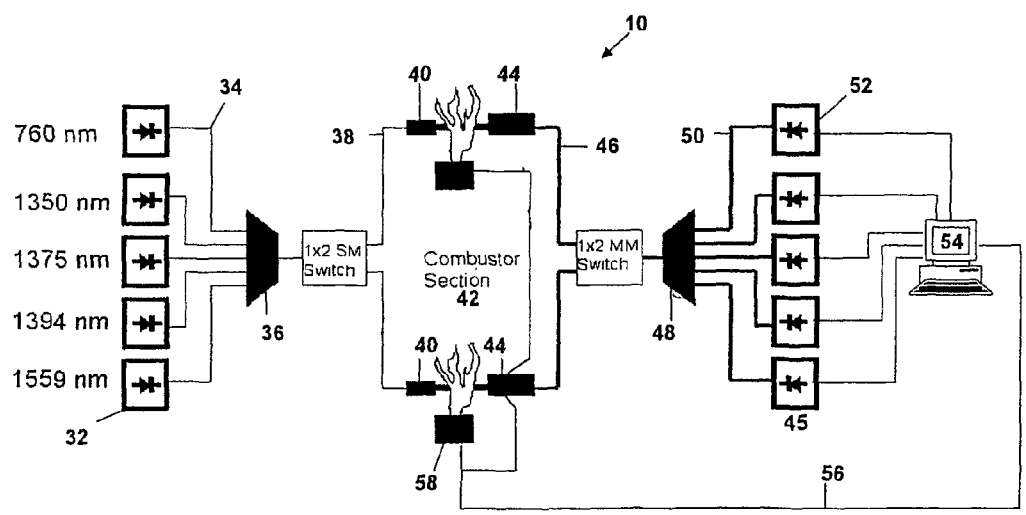
FIG. 2 is a schematic diagram of an apparatus consistent with the present invention featuring remotely located components optically coupled to components near the combustion chamber.

An apparatus 10 suitable for a combustion chamber implementation of the present invention is more specifically described and shown in FIG. 2. The sensing apparatus 10 performs tunable diode laser absorption spectroscopy (TDLAS) using laser light from a series of tunable diode lasers 32 lasing at select frequencies preferably in the near-infrared or mid-infrared spectrum. The output of each tunable diode laser 32 is coupled to an individual optical fiber which may be a single mode optical fiber 34 and routed to a multiplexer 36. As used herein, "coupled", "optically coupled" or "in optical communication with" is defined as a functional relationship between counterparts where light can pass from a first component to a second component either through or not through intermediate components or free space. Within the multiplexer 36 the laser light of some or all of the frequencies generated is multiplexed to form a multiplexed probe beam having multiple select frequencies. The multiplexed probe beam is coupled to a pitch side optical fiber 38 and transmitted to a pitch optic 40 or collimator operatively associated with a process chamber which, in FIG. 2, is shown as a combustion chamber 42.

The pitch optic 40 is oriented to project the multiplexed probe beam through the combustion chamber 42. Across the combustion chamber 42 in optical communication with the pitch optic 40 is a catch optic 44. The catch optic 44 is preferably substantially opposite the pitch optic 40 and is operatively associated with the combustion chamber 42. The catch optic 44 is positioned and oriented to receive the multiplexed probe beam projected through the combustion chamber 42. The catch optic 44 is optically coupled to a catch side optical fiber 46 which transmits the portion of the multiplexed probe beam which is received by the catch optic 44 to a demultiplexer 48. Within the demultiplexer 48 the portion of the multiplexed probe beam received by the catch optic 44 is demultiplexed and each wavelength of demultiplexed laser light is coupled to an output optical fiber 50. Each output optical fiber 50 in turn is optically coupled to a detector 52, which typically is a photodetector sensitive to one of the select frequencies of laser light generated and multiplexed to form the probe beam. The detectors 52 generate an electrical signal based upon the nature and quantity of light transmitted to the detector 52 at the detector frequency. The electrical signal from each detector 52 is typically digitized and analyzed in data processing system 54. As discussed in detail below, the digitized and analyzed data can be used to sense physical parameters within the process chamber including but not limited to the concentrations of various gas species and the combustion temperature within the combustion chamber 42. The data processing system 54 can further be used to send signals through a feedback loop 56 to combustion control apparatus 58 and thereby actively control select process parameters. In the case of a combustion process, the process parameters controlled can include fuel (e.g., pulverized coal) feed rates; oxygen feed rates and catalyst or chemical agent addition rates. The use of fiber optic coupling of the electronic and optical components on both the pitch and catch sides of the sensing apparatus 30 allows delicate and temperature sensitive apparatus such as the tunable diode lasers 32, detectors 52 and data processing system 54 to be located in a control room having a stable operating environment. Thus, only the relatively robust pitch and catch optics 40, 44 need be situated near the hostile environment of the combustion chamber 42.

The present invention may be implemented with any type of gas adsorption spectroscopy, including but not limited to tunable diode laser absorption spectroscopy (TDLAS). TDLAS is performed with techniques known to those skilled in the art of laser spectroscopy. Generally, TDLAS is performed by the transmission of laser light through a target environment, followed by the detection of the absorption of the laser light at specific wavelengths, due to target gases, for example carbon monoxide or oxygen. Spectral analysis of the detected light allows identification of the type and quantity of gas along the laser path. The details of direct absorption spectroscopy are discussed in Teichert, Fernholz, and Ebert, "Simultaneous in situ Measurement of CO, H$_2$O, and Gas Temperature in a Full-Sized, Coal-Fired Power Plant by Near-Infrared Diode Lasers," (Applied Optics, 42(12):2043, 20 Apr. 2003), which reference is incorporated herein in its entirety. The non-contact nature of laser absorption spectroscopy makes it well-suited for harsh environments such as the combustion zone of a coal-fired power plant, or flammable or toxic environments where other probes cannot be used. The use of laser light provides the high brightness necessary to get detectible transmission in the presence of severe attenuation (typically greater than 99.9% loss of light) that may be seen in some of these environments. To better withstand the harsh conditions of the target applications, the laser light may be brought in to the target environment through armored optical fiber.

Effective sensing of the temperature or concentration of multiple combustion process component gasses requires the performance of TDLAS with multiple widely spaced frequencies of laser light. The frequencies selected must match the absorption lines of the transitions being monitored. For example, it may be desired to monitor NO$_2$ at a wavelength of 670 nm to approximate emission NO concentrations. It is also quite useful to monitor oxygen, water and carbon monoxide in a coal-fired utility boiler to extract both temperature and concentration data. In a power plant implementation, suitable absorption lines, and thus suitable lasing frequencies can be selected based upon an assumption that the laser probe path length through a combustion chamber is equal to 10 meters and that the mole fraction of each species is CO (1%), O$_2$ (4%), CO$_2$ (10%), and H$_2$O (10%). For frequency selection purposes, the process temperature can be assumed to be 1800 K which is slightly higher than what is typically observed in a coal fired plant, but the cushion serves as a safety factor in the calculations. Other types of gas absorption spectroscopy implementations will be accompanied by different assumptions.

With respect to the coal fired power plant example, three water absorption lines can be selected for TDLAS that meet the following criteria:
1. Lower state energy of ~1000, 2000, and 3000 cm$^{-1}$ respectively
2. Provides a convenient absorbance of around 0.1-0.4 that, in turn, leads to approximately 20% beam absorption on resonance.
3. The optimum situation is to utilize transitions in the 1250 to 1650 nm region where inexpensive, high power, DFB diode telecommunications lasers are available.
4. The transitions must be well separated to allow for easy multiplexing.
5. The selected wavelength must be efficiently diffracted by the existing (de)multiplexer gratings.

Suitable water lines occur at the following wavelengths:

With respect to water, no interference from any other combustion gases is anticipated The most likely species to interfere, CO$_2$ has been modeled in a power plant setting and there are no strong, interfering lines in the 1.3-1.4 micron region.

Similarly, a suitable carbon monoxide line can be selected based on the work of Ebert referenced and incorporated above. A suitable carbon monoxide line is found at 1559.562 nm using the R(24) line in a coal-fired utility boiler. Selection of this line avoids interference from water and carbon dioxide. Known gratings are quite efficient in this wavelength region since it is in the optical communications C band. The absorbance at this wavelength is expected to be 0.7%.

In addition, oxygen can be measured at 760.0932 nm. The preferred (de)multiplexing grating efficiency calculates to be only 40% in this region, however suitable laser power should be available for reasonable measurement efficiency.

As discussed herein, the use of fiber coupling on both the pitch and catch sides of a TDLAS sensing apparatus requires critical alignment of the pitch and catch optics. Active alignment is preferably accomplished with a select alignment wavelength. One possible alignment wavelength is 660 nm because high power (45 mW) diodes are available at this frequency and 660 nm would be near the peak of 14th order grating operation. Other alignment wavelengths may be determined to be equally or more suitable.

In summary, a reasonable set of wavelengths selected for multiplexing to a probe beam for TDLAS as embodied in the present invention are as shown in Table 2. It should be noted that this wavelength set is for one embodiment of a TDLAS sensing apparatus suitable for the sensing and control of a coal fired power plant. Other wavelength sets can be equally suitable.

TABLE 2

| Purpose | Wavelength (nm) |
|---|---|
| Alignment | 660 |
| O$_2$ b-a band | 760.0932 |
| H$_2$O (moderate temp. line) | 1349.0849 |
| H$_2$O (high temp. line) | 1376.4507 |
| H$_2$O (low temp. line) | 1394.5305 |
| CO R(24) of(2, 0) overtone | 1559.562 |

A particular advantage of TDLAS with a wavelength-multiplexed probe beam is increased accuracy of temperature measurements. In order to make accurate concentration measurements with TDLAS, the temperature of the monitored gas must be known. The strength of a molecular absorption is a function of temperature. Thus, to convert the amplitude of an absorption feature to concentration, the temperature must be known. Certain previous attempts to measure the concentration of combustion species such as CO suffer from insufficiently accurate temperature measurements leading to errors in quantification. This is particularly true for diode laser based ammonia slip monitors that have traditionally not incorporated temperature measurement at all. In the sensing

TABLE 1

| Wavelength (nm) | Wavenumber (cm$^{-1}$) | Lower State Energy (cm$^{-1}$) | Grating Order | Absoprtion at 1800 K and 10 M | UNP Grating Efficiency (model) |
|---|---|---|---|---|---|
| 1349.0849 | 7412.432 | 1806.67 | 6.87 | 19.7% | 81% |
| 1376.4507 | 7265.062 | 3381.662 | 6.73 | 28.1% | 77% |
| 1394.5305 | 7170.872 | 1045.058 | 6.65 | 6.8% | 72% | system of the present invention, temperature may be determined by measuring the ratio of the intensity of two or more molecular water lines. The ratio of the integrated intensity of two lines is a function of temperature only (assuming constant total system pressure). Thus, in principle, two lines provide an accurate temperature. However, in the case of a non-uniform temperature distribution (as is typically found within an industrial combustion process), two lines do not suffice to determine the temperature distribution. In such a non-uniform temperature distribution, two lines can only determine a "path-averaged" temperature. In contrast, measuring the integrated amplitude of more than two lines (of the same species) allows temperature non-uniformity to be probed. An example of this technique has been demonstrated using oxygen as the probe molecule by Sanders, Wang, Jeffries and Hanson in "Applied Optics" (volume 40, number 24, 20 Aug. 2001), which reference is incorporated herein in its entirety. The preferred technique relies on the fact that the distribution of peak intensities measured along a line of sight is not the same for a path at an average temperature of 500 K, for example, as it is where one half of the path is at 300 K and the other half is at 700 K.

In addition to the benefit of more accurate temperature measurement, the use of a multiplexed probe beam can allow for the simultaneous monitoring of more than one combustion gas species, allowing for more refined control over the combustion process.

An important attribute of the application of TDLAS to combustion monitoring and control as described above is the ability to measure $O_2$ levels in the furnace or combustion chamber 12. Many furnace designs include a purge gas supply 20 which helps to keep the openings 14 clear of ash. The purge gas supply 20 is typically constantly flowing during furnace operation and includes significant amounts of $O_2$ relative to the total $O_2$ along the laser path. Depending on the location in the furnace the purge air may include anywhere from 30-60% of the total $O_2$ along the path, though this percentage is constant for a given location. Since it is only the $O_2$ in the furnace which is of interest the additional purge air) $O_2$ must be accurately quantified.

FIG. 1 illustrates in block diagram form the path of the laser light as it first passes through an opening 14 and through the combustion chamber 12. $O_2$ is present in varying concentrations throughout the path. In the following equations, L denotes path length, T is temperature and $X_{O2}$ is the Oxygen concentration. Subscripts P and F denote purge and furnace, respectively.

$$A_1 = F(S_1, X_{O2,F}, X_{O2,P}, E_1, T_F, T_P, L_F, L_P) \quad (1)$$

$$A_2 = F(S_2, X_{O2,F}, X_{O2,P}, E_2, T_F, T_P, L_F, L_P) \quad (2)$$

Absorbances $A_1$ and $A_2$ may be measured with the TDLAS apparatus, and have known functional dependencies on absorption line strength, S, furnace $O_2$ concentration $X_{O2,F}$, purge flow $O_2$ concentration $X_{O2,P}$, lower state absorption line energy, E, furnace temperatures $T_F$, purge flow temperature $T_P$, furnace path length $L_F$ 22 and purge path length $L_P$ 24. Absorption line strengths and lower state energies are know physical constants. Path lengths 22, 24 may be manually measured. A temperature in the combustion chamber 12 may be determined from other measurements (the TDLAS monitoring of two or more water absorption lines in particular). The $O_2$ concentration in the purge gas is typically equal to the ambient concentration, 21%, assuming that outside air is forced through the opening 14 as purge gas. This leaves two unknowns: $X_{O2,F}$ and $T_P$; the $O_2$ concentration in the combustion chamber 12 and the temperature of the purge air.

Two independent equations relating the measured absorbance and the two unknowns may thus be derived by measuring $O_2$ at two distinct absorption lines, each with different line strengths and different lower state energies.

$$A_1 = F_1(X_{O2,F}, T_P) \quad (3)$$

$$A_2 = F_2(X_{O2,F}, T_P) \quad (4)$$

The two (nonlinear) functional relationships (3) and (4) may be solved for the two unknowns $X_{O2,F}$ and $T_P$ by measuring the absorbances $A_1$ and $A_2$. Then, the relationship between $X_{O2,F}$ and $T_P$ may be constructed and solved using a nonlinear solution method such as the Newton-Raphson method The Newton-Raphson method and other methods of solving multiple nonlinear functional relationships use an iterative process to approach possible roots of the functions. The result will be two curves, the intersection of which determines the values of $X_{O2,F}$ and $T_P$ that simultaneously solve equations (3) and (4).

Figure 3:
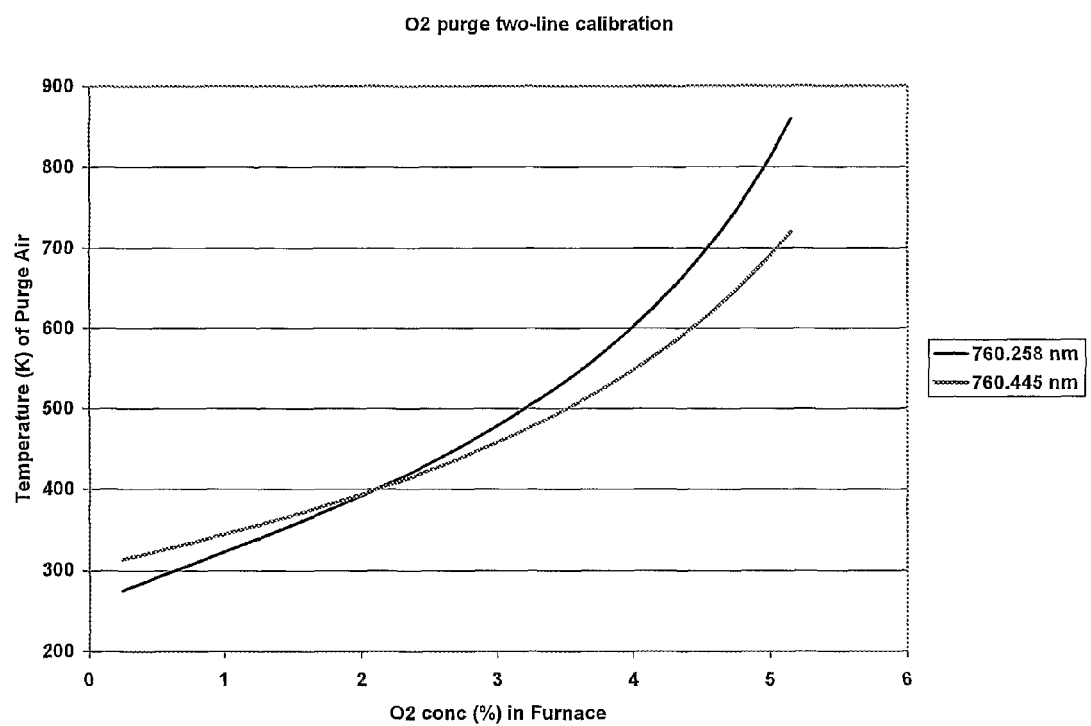
FIG. 3 is a graphical illustration of a calibration consistent with the present invention.

FIG. 3 is a representation of a solution to equations (3) and (4). FIG. 3 demonstrates two curves relating purge air temperature to furnace $O_2$ concentration as measured at two different $O_2$ lines located near the 760 nm $O_2$ absorption band head. The measurements, which are represented in FIG. 2, were made at an active coal fired power plant. The intersection point shown in FIG. 3 indicates a purge air temperature of 400 K and a furnace $O_2$ concentration of 2.1%.

The curves in FIG. 3 are the results of the calibration approach of the present invention being applied to an installation measured while the combustion settings were steady state. The present invention is particularly well suited to $O_2$ determinations under dynamic operating conditions as well.

The example set forth in detail above concerns the calibration of a TDLAS measurement of $O_2$ in a power plant combustion chamber setting. The calibration method is particularly useful since supplemental $O_2$ is typically introduced through a purge gas supply, which will complicate the desired measurement. The method described above is applicable to any gas absorption spectroscopy implementation where the probe laser is transmitted across both a region containing the gas of interest, and a region containing supplemental gas which would otherwise skew the spectroscopic analysis.

While the invention has been particularly shown and described with reference to a number of embodiments, it would be understood by those skilled in the art that changes in the form and details may be made to the various embodiments disclosed herein without departing from the spirit and scope of the invention and that the various embodiments disclosed herein are not intended to act as limitations on the scope of the claims.

What is claimed is:

1. A method of calibrating an absorption spectroscopy measurement comprising:
   projecting laser light through a sample containing a first quantity of a gas of interest and a second quantity of a spectroscopically identical or similar gas;
   measuring a first spectroscopic absorption of the laser light over a first select absorption line;
   measuring a second spectroscopic absorption of the laser light over a second select absorption line;
   determining a first functional relationship between the first measured spectroscopic absorption and two unknown variables;
   determining a second functional relationship between the second measured spectroscopic absorption and the two unknown variables; and simultaneously solving the first functional relationship and the second functional relationship to determine information concerning the first quantity of the gas of interest.

2. The method of claim 1 further comprising:
calculating a mean temperature within the first quantity of the gas of interest;
measuring a path length through the first quantity of the gas of interest;
measuring a second path length through the second quantity of the spectroscopically identical or similar gas; and
determining the first and second functional relationships with respect to the measured temperature within the first quantity of the gas of interest, the measured path length through the first quantity of the gas of interest and the measured path length through the second quantity of a spectroscopically identical or similar gas.

3. The method of claim 2 further comprising determining the first and second functional relationships with respect to known physical constants selected from a group of constants including:
a first select absorption line strength associated with the first select absorption line;
a second select absorption line strength associated with the second select absorption line;
a lower energy state associated with the first select absorption line;
a lower energy state associated with the second select absorption line; and
a gas concentration of the gas of interest contained within the second quantity of the spectroscopically identical or similar gas.

4. A method of determining the $O_2$ concentration within a combustion chamber by tunable diode laser absorption spectroscopy (TDLAS) where at least one laser is positioned to transmit laser light through at least one opening into the combustion chamber and where an $O_2$ containing purge gas flow is applied to the opening, the method comprising:
projecting laser light through the opening and through the combustion chamber;
measuring a first spectroscopic absorption of the laser light over a first select $O_2$ absorption line;
measuring a second spectroscopic absorption of the laser light over a second select $O_2$ absorption line;
determining a first functional relationship between the first measured spectroscopic absorption and two unknown variables;
determining a second functional relationship between the second measured spectroscopic absorption and the two unknown variables; and
simultaneously solving the first functional relationship and the second functional relationship to determining the $O_2$ concentration within the combustion chamber.

5. The method of determining the $O_2$ concentration within a combustion chamber of claim 4 wherein the two unknown variables are a temperature of the $O_2$ containing purge gas and the $O_2$ concentration with in the combustion chamber.

6. The method of claim 4 further comprising:
calculating a mean temperature within the combustion chamber;
measuring a path length through the combustion chamber;
measuring a purge path length associated with the opening; and
determining the first and second functional relationships with respect to the measured temperature within the combustion chamber, the measured path length through the combustion chamber and the measured purge path length.

7. The method of claim 6 further comprising determining the first and second functional relationships with respect to known physical constants selected from a group of constants including:
a first select $O_2$ absorption line strength associated with the first select $O_2$ absorption line;
a second select $O_2$ absorption line strength associated with the second select $O_2$ absorption line;
a lower energy state associated with the first select $O_2$ absorption line;
a lower energy state associated with the second select $O_2$ absorption line; and
an $O_2$ concentration of the $O_2$ containing purge gas flow.

8. The method of claim 6 further comprising calculating the temperature within the combustion chamber from an absorption spectra measured over at least two $H_2O$ absorption lines.

9. The method of claim 4 wherein the first select $O_2$ absorption line corresponds to absorption of light having a wavelength of 760.258 mm and the second select absorption line corresponds to absorption of light having a wavelength of 760.445 nm.

10. An apparatus for determining the $O_2$ concentration within a combustion chamber comprising:
at least one opening into the combustion chamber;
a tunable diode laser positioned to transmit laser light through the opening and the combustion chamber;
a source of $O_2$ containing purge gas in fluid communication with the opening;
means for measuring a first spectroscopic absorption of the laser light over a first select $O_2$ absorption line;
means for measuring a second spectroscopic absorption of the laser light over a second select $O_2$ absorption line;
means for determining a first functional relationship between the first measured spectroscopic absorption and two unknown variables: a temperature of the $O_2$ containing purge gas and the $O_2$ concentration with in the combustion chamber;
means for determining a second functional relationship between the second measured spectroscopic absorption and the two unknown variables; and
means for simultaneously solving the first functional relationship and the second functional relationship to determine the $O_2$ concentration within the combustion chamber.

* * * * *